United States Patent
Tockman et al.

[19]

[11] Patent Number: 6,033,414

[45] Date of Patent: Mar. 7, 2000

[54] TORQUE DEVICE FOR LEFT VENTRICULAR LEAD SYSTEMS

[75] Inventors: Bruce A. Tockman, Scandia; Randy Westlund, Minneapolis, both of Minn.

[73] Assignee: Cardiac Pacemakers, Inc., St. Paul, Minn.

[21] Appl. No.: 09/100,164

[22] Filed: Jun. 18, 1998

[51] Int. Cl.[7] .................................................. A61N 1/36
[52] U.S. Cl. .......................................... 606/129; 607/122
[58] Field of Search ........................... 607/122; 606/129; 604/158, 159

[56] References Cited

U.S. PATENT DOCUMENTS

| | | | |
|---|---|---|---|
| 3,312,128 | 4/1967 | Wasson | 81/487 |
| 3,452,740 | 7/1969 | Muller | 600/585 |
| 4,351,345 | 9/1982 | Carney | 607/122 |
| 4,886,065 | 12/1989 | Collins, Jr. | 600/377 |
| 4,957,117 | 9/1990 | Wysham | 604/95 |
| 5,041,085 | 8/1991 | Osborne et al. | 604/51 |
| 5,137,288 | 8/1992 | Starkey et al. | 604/159 |
| 5,137,517 | 8/1992 | Loney et al. | 604/159 |
| 5,161,534 | 11/1992 | Berthiaume | 128/657 |
| 5,228,441 | 7/1993 | Lundquist | 128/642 |
| 5,261,892 | 11/1993 | Bertaud et al. | 604/171 |
| 5,325,746 | 7/1994 | Anderson | 81/487 |
| 5,328,467 | 7/1994 | Edwards et al. | 604/95 |
| 5,329,923 | 7/1994 | Lundquist | 128/642 |
| 5,374,252 | 12/1994 | Banks et al. | 604/158 |
| 5,423,884 | 6/1995 | Nyman et al. | 607/122 |
| 5,439,006 | 8/1995 | Brennen et al. | 128/772 |
| 5,478,330 | 12/1995 | Imran et al. | 604/282 |
| 5,487,757 | 1/1996 | Truckai et al. | 607/122 |
| 5,522,875 | 6/1996 | Gates et al. | 607/127 |
| 5,611,777 | 3/1997 | Bowden et al. | 604/95 |
| 5,693,015 | 12/1997 | Walker et al. | 604/96 |
| 5,803,928 | 9/1998 | Tockman et al. | 607/122 |
| 5,827,272 | 10/1998 | Breining et al. | 606/41 |
| 5,851,189 | 12/1998 | Forber | 600/585 |
| 5,865,800 | 2/1999 | Mirarchi et al. | 604/95 |
| 5,897,584 | 4/1999 | Herman | 607/122 |
| 5,938,616 | 8/1999 | Eaton et al. | 600/463 |
| 5,964,753 | 10/1999 | Edwards | 606/33 |
| 5,987,344 | 11/1999 | West | 600/373 |

*Primary Examiner*—Paul J. Hirsch
*Assistant Examiner*—Michael B. Priddy
*Attorney, Agent, or Firm*—Nikolai, Mersereau & Dietz, P.A.

[57] ABSTRACT

The present invention is a torque handle for use in inserting and positioning a pacing lead and guide wire, such as within a coronary vein. The torque handle is a handle with a lumen extending therethrough. A first clamping arrangement is located on the handle and receives the guide wire therethrough. A second clamping arrangement is also located on the handle. The second clamping arrangement sized to receive the body of the lead therethrough. In use, the physician determines whether torque is to be transmitted along the lead, the guide wire or both. Torque is transmitted by clamping or loosening the designated clamping arrangement around the lead, the guide wire or both, and then rotating the handle. As the handle is rotated, torque is transmitted along the length of the clamped lead or guide wire or both.

6 Claims, 1 Drawing Sheet

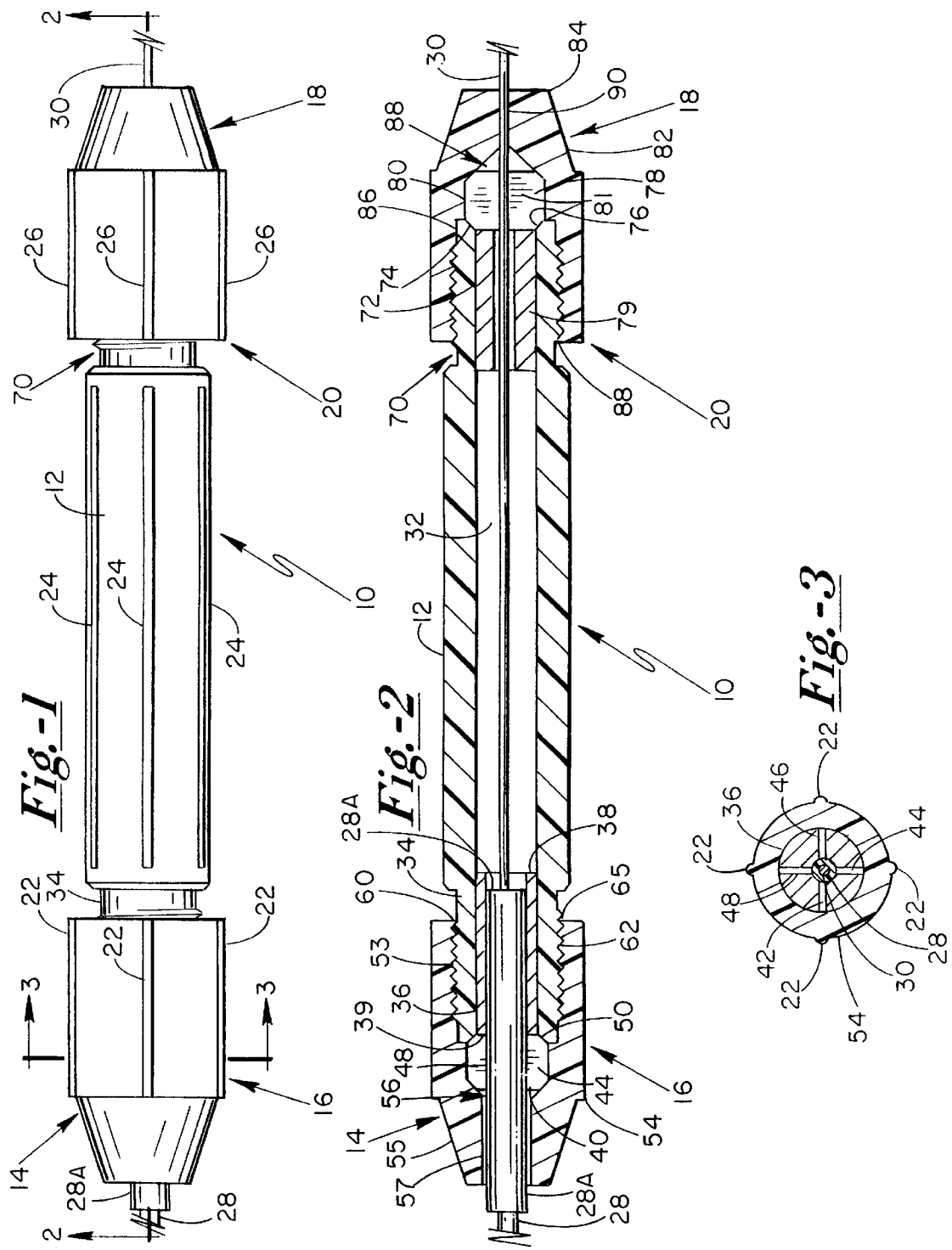

TORQUE DEVICE FOR LEFT VENTRICULAR LEAD SYSTEMS

FIELD OF INVENTION

The present invention relates to pacing leads and more particularly to a torque device for use in the installation and positioning of a pacing lead.

BACKGROUND OF THE INVENTION

Cardiac pacemakers for treating bradycardia commonly employ pacing leads for connecting an electrical pulse generator to excitable cardiac tissue, usually within the heart's right ventricle. Such leads have one or more electrodes proximate the distal end thereof and also commonly employ tines located just distal of the tip electrode for holding that electrode in contact with endocardial tissue in the right ventricle. The tines engage the trabeculae, resisting movement of the lead tip due to body movement and/or contractions of the heart muscle itself.

More recently, researchers have found that cardiac stimulation can have a beneficial effect in treating patients suffering from congestive heart failure (CHF). By properly controlling the AV interval of the pacemaker, a sick heart may be made to pump more efficiently. Pacing therapy for the treatment of CHF, however, often requires the ability to stimulate the left ventricle, either alone or in conjunction with right ventricular stimulation. Current methods for achieving left ventricular pacing require placement of an epicardial lead, via thoracotomy or a thoracoscopic approach. Because of the usual poor condition of CHF patients, both of these procedures are "high risk" due to the trauma of the surgery itself and the need for general anesthesia. To obviate the need for a thoracotomy, left ventricular access (LVA) leads have been developed that may be introduced through the coronary sinus and then advanced through the coronary veins so that the lead's stimulating tip electrode can be positioned on the surface of the left ventricle near the apex of the heart.

It is sometimes difficult to feed an endocardial or intravenous lead along the desired predetermined path to implant the electrode or electrodes in a desired implantation site, either in a chamber of the heart or in a selected coronary vein. This is especially true for routing leads through the coronary sinus and into a branching vein on the left myocardium. The difficulties often are a result of anomalies in the vascular anatomy and the number of veins encountered when locating the desired path. Furthermore, controlling the LVA lead's movement is difficult because of the long tubular structure of a lead and its corresponding stylet/guide wire. The stylet/guide wire has to be rigid enough to afford pushability to the lead and provide navigation of the lead so as to arrive at the desired location. In addition, there must be enough torque control so that by twisting the lead at its proximal end, torque will then be transmitted along the lead to its distal end. However, existing devices do not allow the physician to selectively torque only the stylet or only the lead or both when positioning the lead. Thus, a need exists to have a torque device which allows independent torquing of the lead and stylet along with the ability to torque the stylet and lead together.

SUMMARY OF THE INVENTION

The present invention is a torque device for positioning leads, and in particular, the type of lead used for pacing the left ventricle. The pacing lead must be routed through the patient's coronary sinus and great cardiac vein into a select vein that branches off on the left ventricular surface of the patient's heart. The lead comprises an elongated conductive wire or cable wound as a helix to define a central lumen and covered with an insulative jacket or coating. It has one or more electrodes at its distal end and one or more terminal pins at its proximal end adapted to be connected to a pacemaker. The torque device comprises a tubular handle, open on each end, and adapted to be affixed to the proximal end of a lead and guide wire arrangement. A lumen extends through the handle. A guide wire or stiffening stylet extends through the lumen of the handle from a first end thereof and into the lumen of the lead through the terminal end of the lead located at the second end of the handle. The proximal end, or guide wire end, has a clamping arrangement comprising a collet and chuck for selectively clamping the guide wire and thereby allowing the guide wire, once clamped, to be advanced or withdrawn within the lead lumen or torqued by rotating the handle. The distal end, or lead end, also has a clamping arrangement comprising a collet and chuck for selectively clamping the lead. Once clamped, the lead can then be advanced along the guide wire and torqued by rotating the handle.

When both the lead and guide wire are secured in their respective clamping arrangements, the handle may be rotated providing torque to both the lead and the guide wire along their length and both may be simultaneously advanced or withdrawn within the vasculature. In the event that the operator needs to only maneuver the lead, the clamping arrangement around the guide wire is released. The handle may then be manipulated, transmitting torque or axial forces only to the lead. In the event that the operator only needs to maneuver the guide wire, the clamping arrangement surrounding the guide wire is engaged and the clamping arrangement surrounding the lead end is released. Manipulation of the torque handle will then only transmit forces along the length of the guide wire.

OBJECTS OF THE PRESENT INVENTION

The primary object of the present invention is to provide a torque device that allows the user to selectively transmit torque and/or axial forces along the length of a pacing lead, its guide wire or both.

Another object of the present invention is to provide a torquing device adapted to be attached to the proximal end of the lead to enable the user to selectively transmit axial force along the length of the lead, or its guide wire/stiffening stylet or both the lead and guide wire/stiffening stylet as a unit.

DESCRIPTION OF THE DRAWINGS

These and other objects and advantages of the present invention will become readily apparent to those skilled in the art from the review of the following detailed description of the preferred embodiment especially when considered in conjunction with the accompanying drawings in which like numerals and the several views refer to the corresponding parts:

FIG. 1 is a side elevational view of the present invention;

FIG. 2 is a cross sectional view taken along line 2—2 of FIG. 1; and

FIG. 3 is a cross sectional view of the present invention taken along line 3—3 of FIG. 1.

DETAILED DESCRIPTION OF THE PREFERRED EMBODIMENT

The present invention is a torque handle designated generally as 10 in FIG. 1, adapted to be used for selectively applying torque and axial force to a pacing lead during placement thereof. The torque handle 10 consists of an intermediate handle portion 12 with a distal or lead end 14 to which a lead body clamping arrangement 16 is affixed and a proximal or guide wire end 18 to which a guide wire clamping arrangement 20 is affixed. The torque handle 10 can include raised areas, such as those designated as 22, 24 and 26, to assist in gripping and operating the torque handle 10. A pacing lead 28 is shown as extending from the lead end 14 of handle 10, and a guide wire, or stiffening stylet, 30 is shown extending from the proximal or guide wire end 18.

Turning now to FIG. 2, the interior of the torque handle 10 will be described in greater detail. A tubular lumen 32 extends through the length of torque handle 10. The lead end 14 has a reduced outer diameter portion 34 which is threaded as seen in FIG. 2. A tubular collet 36 is positioned with its first end, collet body 38, within the lumen 32 of the torque handle 10. Its second end, collet head 40, extends outward from the lumen 32 of the intermediate handle portion 12. Edge 50 surrounding the lumen opening is tapered to match a taper 39 formed on head 40 of collet 36. This allows collet 36 to be firmly seated in the handle 10. The collet's interior diameter is sized to receive the body of the lead 28 therethrough and its terminal pin connector 28a. The head 40 of the collet has a plurality of equally spaced radial slots 42, 44, 46 and 48 (FIG. 3) that extend longitudinally from the outer end 40 of the collet towards its middle. The slots 42, 44, 46 and 48 allow the collet head 40 to compress inwardly to clamp the lead body 28 as will be explained in greater detail with respect to the operation of the torque handle 10.

Surrounding collet 36 and reduced diameter portion 34 of the handle member 12 is a chuck 54 for distal or lead end 14. The chuck 54 is cylindrical over a major portion but having a frusto-conical end 55. It includes a central bore 53 that is threaded on its interior surface to mate with threads on the outer surface 34 of the handle member 12. A tapered counter bore 56 is formed which is sized to receive the tapered end of the collet head 40 and a further cylindrical bore 57, concentric with the central bore 53, extends through the frusto-conical end portion 55. Chuck 54 includes raised areas on its exterior, such as those designated 22 in FIG. 1, to assist the user in manipulating the chuck 54. As the chuck 54 is rotated towards the intermediate portion 12 of torque handle 10, the counter bore 56 compresses the collet 36. Collet head 40 thus closes around the lead 28 to firmly secure and clamp the lead terminal pin 28A.

The proximal or guide wire end 18 of torque handle 10 has a clamping arrangement similar to what is on the distal or lead end 14. It has a reduced diameter portion 70. A tubular collet 72 extends into the lumen 32 and the bore in its head portion 78 is sized to receive the guide wire 30 therethrough. Guide wire end 18 has a tapered edge 74 that corresponds to tapered surface 76 on collet head 78 to permit the collet 72 to firmly seat in the torque handle 10. The collet 72, like collet 36, has radial slots extending through its head 78 from an end thereof to an intermediate location on its body 79. Two such slots are shown as 80 and 81 in FIG. 2.

Surrounding collet 72 and reduced diameter portion 70 of the handle 12 is chuck 82 for proximal or guide wire end 18. The chuck 82 is cylindrical over a major portion but having a frusto-conical end 84. It includes a central bore 86 that is threaded on its interior surface to mate with threads on the outer surface 70 of the handle member 12. A tapered counter bore 88 is formed which is sized to receive the tapered end of the collet head 78 and a further cylindrical bore 90, concentric with the central bore 86, extends through the frusto-conical end portion 84. Chuck 82 includes raised areas on its exterior, such as those designated 26 in FIG. 1, to assist the user in manipulating the chuck 82. As the chuck 82 is screwed towards the intermediate portion 12 of torque handle 10, the counter bore 86 compresses the collet 72. Collet head 78 closes around the guide wire 30 to firmly secure and clamp the guide wire. While the preferred embodiment shows the clamping arrangements on either end of the handle, the clamping arrangements can be positioned adjacent each other on the handle.

The operation of the device will now be described. The terminal end 28a of lead 28 is positioned within the collet 36 with the lead 28 and terminal end 28a extending through the opening on the chuck 54. As seen in FIG. 2, the guide wire 30 is routed through lumen 32 from guide wire end 18 of torque handle 10 and into the lumen (not shown) of the lead 28. The physician then determines whether torque control is desired with the lead 28, the guide wire 30 or both. If the physician chooses to have torquing capabilities with only the lead 28, chuck 54 is tightened to compress collet head 40 about the lead 28. Chuck 82 at the guide wire end 18 is loosened so that it does not compress collet 72 about the guide wire 30. The physician is then able to rotate the torque handle 10 to transmit torque and apply axial force along the length of the lead 28.

If the physician chooses to transmit torque or axial force only along the guide wire 30, chuck 54 is loosened around the collet 36 securing the lead 28 until the lead is no longer clamped within the collet 36. Chuck 82 is then tightened about the collet 72 until it clamps the guide wire 30 securely. The physician is then able to rotate the torque handle 10 to transmit torque or apply axial force along the length of the guide wire 30.

In the event that the physician wishes to transmit the torque or force along the length of both the lead 28 and guide wire 30, both chucks, 54 and 82, are tightened about their respective collets, 36 and 72, to firmly clamp the lead 28 and guide wire 30. Rotation of the torque handle 10 then twists both the stiffening stylet/guide wire 30 and the lead body 28 together as a unit and axial force advances or withdraws both together as a unit.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A torque handle for use in positioning a lead and guide wire arrangement used with a cardiac stimulating lead, said torque handle comprising:

(a) a handle member with a lumen extending therethrough;

(b) a first clamping arrangement on said handle member, said first clamping arrangement sized to receive said lead therethrough and being selectively clamped onto said lead; and (c) a second clamping arrangement on said handle member, said second clamping arrangement sized to receive said guide wire therethrough and being selectively clamped onto said guide wire.

2. A torque handle of claim 1 wherein said first clamping arrangement is configured to receive a terminal end of said lead.

3. A torque handle of claim 1 wherein said first clamping arrangement comprises a chuck and corresponding collet.

4. A torque handle of claim 1 wherein said second clamping arrangement comprises a chuck and corresponding collet.

5. A torque handle of claim 3 wherein said second clamping arrangement comprises a chuck and corresponding collet.

6. A torque handle used in the insertion and positioning of a cardiac stimulating lead and guide wire, said torque handle comprising:

(a) a handle with a lumen extending therethrough, said handle adapted to be affixed to a proximal end of said lead and guide wire, said lumen receiving said lead and guide wire therewithin, (b) a first threaded end on said handle member;

(b) a second threaded end on said handle member;

(c) a first collet inserted into said lumen and extending out from said first threaded end;

(d) a first chuck surrounding said first threaded end and said first collet, said first chuck having a threaded internal bore for mating with said first threaded end of said handle member whereby said first chuck may be selectively rotated between a first position compressing said first collet about said guide wire and a second position not compressing said first collet about said guide wire;

(e) a second collet inserted into said lumen on said second threaded end of said handle member and extending out from said threaded end; and (d) a second chuck surrounding said second threaded end and said second collet, said second chuck having a threaded internal bore for mating with said second threaded end of said handle member whereby said second chuck may be selectively rotated to a third position compressing said second collet about said lead and a fourth position not compressing said second collet about said lead.

* * * * *